United States Patent [19]

Skidmore et al.

[11] Patent Number: 5,066,678
[45] Date of Patent: Nov. 19, 1991

[54] PHENETHANDAMINE DERIVATIVES AND PHARMACEUTICAL USE THEREOF

[75] Inventors: Ian F. Skidmore, Welwyn; Lawrence H. C. Lunts, Broxbourne; Harry Finch, Letchworth; Alan Naylor, Royston; Ian B. Campbell, Dane End; Charles Willbe, Bishop's Stortford; William L. Mitchell, London; Stephen Swanson; Brian D. Judkins, both of Ware, all of England

[73] Assignee: Glaxo Group Limited, London, England

[21] Appl. No.: 512,874

[22] Filed: Apr. 23, 1990

[30] Foreign Application Priority Data

Apr. 24, 1989 [GB] United Kingdom ............... 8909273

[51] Int. Cl.$^5$ ................ A61K 31/135; C07C 215/60
[52] U.S. Cl. .................... 514/597; 514/600;
514/605; 514/629; 514/630; 514/653; 564/51;
564/56; 564/79; 564/99; 564/220; 564/361;
564/365
[58] Field of Search ............ 564/51, 56, 79, 99,
564/220, 361, 365; 514/597, 600, 605, 629, 630,
653

[56] References Cited

U.S. PATENT DOCUMENTS

| | | | |
|---|---|---|---|
| 2,900,415 | 8/1959 | Biel | 564/361 |
| 4,396,627 | 8/1983 | Ainsworth et al. | 424/309 |
| 4,404,222 | 9/1983 | Baker et al. | 514/238.8 |

FOREIGN PATENT DOCUMENTS

| | | |
|---|---|---|
| 0181709 | 5/1986 | European Pat. Off. |
| 0223410 | 5/1987 | European Pat. Off. |
| 0286242 | 3/1988 | European Pat. Off. |
| 0288867 | 4/1988 | European Pat. Off. |
| 0278727 | 8/1988 | European Pat. Off. |
| 993584 | 5/1965 | United Kingdom |
| 1178191 | 1/1970 | United Kingdom |
| 1200886 | 8/1970 | United Kingdom |
| 1214012 | 11/1970 | United Kingdom |
| 2140800A | 12/1984 | United Kingdom |
| 2162842A | 2/1986 | United Kingdom |

Primary Examiner—Richard L. Raymond
Attorney, Agent, or Firm—Morgan & Finnegan

[57] ABSTRACT

The invention relates to compounds of the general formula (I)

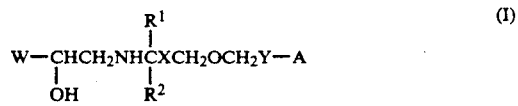

and physiologically acceptable salts and solvates thereof;

wherein;

$R^1$ and $R^2$ each independently represent a hydrogen atom or a $C_{1-3}$-alkyl group with the proviso that the sum total of carbon atom in $R^1$ and $R^2$ is not more than 4;

X represents a direct bond or a $C_{1-7}$alkylene, $C_{2-7}$alkenylene or $C_{2-7}$alkynylene group and Y represents a direct bond or a $C_{1-6}$alkylene $C_{2-6}$alkenylene or $C_{2-6}$alknylene group with the proviso that the sum total of carbon atoms in X and Y is not more than 10;

W represents a group

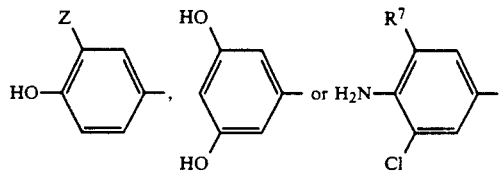

wherein Z represents a group $R^3(CH_2)_q$ where q is 0, 1 or 2 and $R^3$ is a group $R^4CONH—$, $R^4NHCONH—$, $R^4R^5NSO_2NH—$, $R^6SO_2NH—$ or $—OH$;

$R^4$ and $R^5$ each represent a hydrogen atom or a $C_{1-3}$alkyl group;

$R^6$ represents a $C_{1-3}$alkyl group;

$R^7$ represents a chlorine atom or the group $—CF_3$;

A represents a straight or branched $C_{1-6}$alkyl group, a $C_{3-8}$cycloalkyl group, either of which may be saturated or unsaturated, or a $C_{1-6}$alkoxy group, with the proviso that the sum total of carbon atoms in A and Y is not less than 5;

having a stimulant action at $\beta_2$-adrenoreceptors and are useful in the treatment of diseases associated with reversible airways obstruction such as asthma and chronic bronchitis.

28 Claims, No Drawings

PHENETHANDAMINE DERIVATIVES AND PHARMACEUTICAL USE THEREOF

This invention relates to phenethanolamine derivatives having a stimulant action at $\beta_2$-adrenoreceptors, to processes for their preparation, to pharmaceutical compositions containing them and to their use in medicine.

Thus the present invention provides compounds of general formula (I)

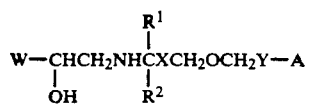
(I)

and physiologically acceptable salts and solvates thereof, wherein $R^1$ and $R^2$ each independently represent a hydrogen atom or a $C_{1-3}$alkyl group with the proviso that the sum total of carbon atoms in $R^1$ and $R^2$ is not more than 4;

X represents a bond or a $C_{1-7}$alkylene, $C_{2-7}$alkenylene or $C_{2-7}$alkynylene group and Y represents a bond or a $C_{1-6}$alkylene, $C_{2-6}$alkenylene or $C_{2-6}$alkynylene group with the proviso that the sum total of carbon atoms in X and Y is not more than 10;

W represents a group

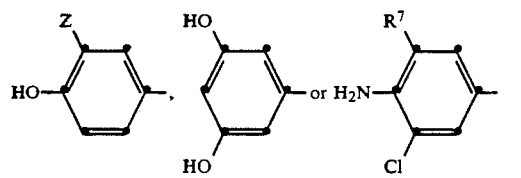

where Z represents a group $R^3(CH_2)_q$ where q is 0, 1 or 2 and $R^3$ is a group $R_4CONH-$, $R_4NHCONH-$, $R_4R_5NSO_2NH-$, $R_6SO_2NH$ or $-OH$;

$R^4$ and $R^5$ each represent a hydrogen atom or a $C_{1-3}$alkyl group;

$R^6$ represents a $C_{1-3}$alkyl group;

$R^7$ is a chlorine atom or the group $-CF_3$;

A represents a straight or branched $C_{1-6}$alkyl group, a $C_{3-8}$ cycloalkyl group, either of which may be saturated or unsaturated, or a $C_{1-6}$alkoxy group, with the proviso that the sum total of carbon atoms in A and Y is not less than 5.

It will be appreciated that the compounds of general formula (I) possess at least one asymmetric carbon atom. The compounds according to the invention thus include all enantiomers, diastereomers and mixtures thereof, including racemates. Compounds in which the carbon atom in the —CH(OH)— group is in the R configuration are preferred.

As used herein the term alkenylene includes both cis and trans structures.

Conveniently $R^1$ and $R^2$ each represent a hydrogen atom or a methyl group. In particular, $R^1$ and $R^2$ conveniently both represent hydrogen atoms.

The chain X may be, for example, —(CH$_2$)$_3$—, —(CH$_2$)$_4$—, —(CH$_2$)$_5$—, —(CH$_2$)$_2$CH=CH—, —(CH$_2$)$_2$C≡C—, —CH=CH(CH$_2$)$_2$— or CH$_2$C≡CCH$_2$—.

The chain Y may be, for example, a bond, —CH$_2$—, —(CH$_2$)$_2$—, —(CH$_2$)$_3$—, —(CH$_2$)$_4$—, —(CH$_2$)$_5$—, —CH$_2$CH=CH— or —CH$_2$C≡C—.

Preferably the sum total of carbon atoms in chains X and Y is 4 to 9 inclusive. Conveniently the number of carbon atoms in the chain X is 4.

In the definition of W in compounds of formula (I), Z may conveniently represent, for example, HOCH$_2$—, HCONH—, NH$_2$CONH— or CH$_3$SO$_2$NH—.

W may represent, for example:

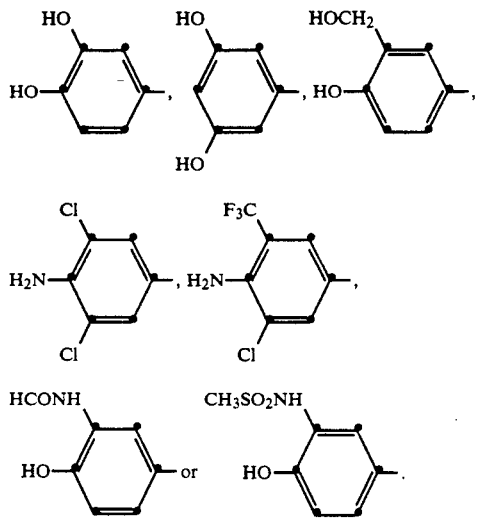

Conveniently, W represents a group

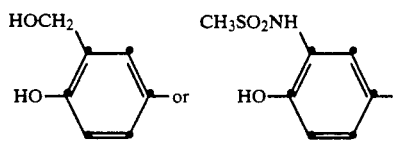

The group A may be, for example —CH$_3$, —CH$_2$CH$_3$, —CH(CH$_3$)$_2$, —C(CH$_3$)$_3$, —CH$_2$CH$_2$CH$_3$, —(CH$_2$)$_3$CH$_3$, —CH(CH$_2$CH$_3$)$_2$, cyclopentyl, cyclohexyl, —OCH$_3$, —OCH$_2$CH$_3$, —O(CH$_2$)$_2$CH$_3$, —O(CH$_2$)$_3$CH$_3$, —OC(CH$_3$)$_3$ or —OCH(CH$_3$)$_2$. Conveniently A represents cyclohexyl or —O(CH$_2$)$_3$CH$_3$.

Preferred compounds according to the invention are those in which $R^1$ and $R^2$ each represent a hydrogen atom and W represents a group

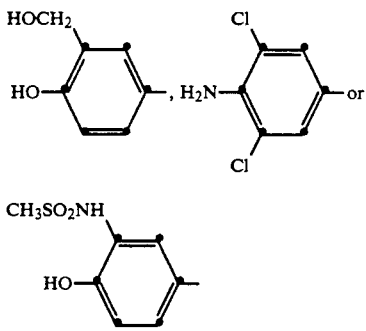

Compounds according to the invention wherein W represents a group

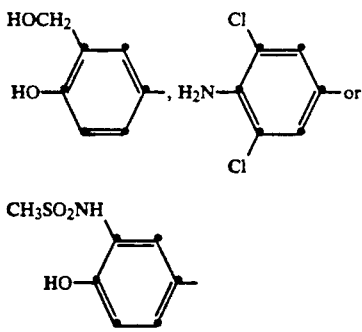

and A represents a cyclohexyl or —O(CH$_2$)$_3$CH$_3$ group are preferred.

Compounds according to the invention wherein R$^1$ and R$^2$ are both hydrogen atoms and the sum total of carbon atoms in the chains X and Y is 4, 5, 6, 7, 8 or 9 are preferred.

Preferred compounds according to the invention include:

α$^1$-[[[6-[2-(cyclopentyl)ethoxy]hexyl]amino]methyl]-4-hydroxy-1,3-benzenedimethanol;

α$^1$-[[[6-(cyclohexylmethoxy)hexyl]amino]methyl]-4-hydroxy-1,3-benzenedimethanol;

α$^1$-[[[6-[2-(cyclohexyl)ethoxy]hexyl]amino]methyl]-4-hydroxy-1,3-benzenedimethanol;

α$^1$-[[[6-[(3-ethylpentyl)oxy]hexyl]amino]methyl]-4-hydroxy-1,3-benzenedimethanol;

α$^1$-[[[6-[(4,4-dimethylpentyl)oxy]hexyl]amino]methyl]-4-hydroxy-1,3-benzenedimethanol;

α$^1$-[[[6-[(hexyl)oxy]hexyl]amino]methyl]-4-hydroxy-1,3-benzenedimethanol;

N-[5-[[[6-[2-(cyclohexyl)ethoxy]hexyl]amino]-1-hydroxyethyl]-2-hydroxyphenyl]methanesulphonamide;

N-[2-hydroxy-5-[2-[[6-[(3-ethylpentyl)oxy]hexyl]amino]-1-hydroxyethyl]phenyl]methanesulphonamide;

α$^1$-[[[6-(heptyloxy)hexyl]amino]methyl]-4-hydroxy-1,3-benzenedimethanol;

4-hydroxy-α$^1$-[[[6-[(5-methylhexyl)oxy]hexyl]amino]methyl]-1,3-benzenedimethanol;

4-amino-3,5-dichloro-α-[[[6-(4-propoxybutoxy)hexyl]amino]methyl]benzenemethanol;

4-amino-α-[[[6-(3-butoxypropoxy)hexyl]amino]methyl]-3,5-dichloro benzenemethanol;

and their physiologically acceptable salts and solvates.

Suitable physiologically acceptable salts of the compounds of general formula (I) include acid addition salts derived from inorganic and organic acids, such as hydrochlorides, hydrobromides, sulphates, phosphates, maleates, tartrates, citrates, benzoates, 4-methoxy-benzoates, 2- or 4-hydroxybenzoates, 4-chlorobenzoates, benzenesulphonates, p-toluenesulphonates, naphthalenesulphonates, methanesulphonates, sulphamates, ascorbates, salicylates, acetates, diphenylacetates, triphenylacetates, adipates, fumarates, succinates, lactates, glutarates, gluconates, tricarballylates, hydroxynaphthalenecarboxylates e.g. 1-hydroxy or 3-hydroxy-2-naphthalenecarboxylates, or oleates. The compounds may also form salts with suitable bases where appropriate. Examples of such salts are alkali metal (e.g. sodium and potassium) and alkaline earth metal (e.g. calcium or magnesium) salts, and salts with organic bases (e.g. triethylamine).

The compounds according to the invention have a stimulant action at β$_2$-adrenoreceptors, which furthermore is of a particularly advantageous profile. The stimulant action was demonstrated in the isolated trachea of the guinea-pig, where compounds were shown to cause relaxation of contractions induced by PGF$_2$α or electrical stimulation. A prolonged duration of action has also been observed.

The compounds according to the invention may be used in the therapy or prophylaxis of conditions susceptible to amelioration by a compound possessing selective stimulant action at β$_2$-adrenoreceptors, particularly of diseases associated with reversible airways obstruction such as asthma and chronic bronchitis. Further examples of conditions which may be alleviated by administration of a compound possessing selective β$_2$-stimulant activity are inflammatory and allergic skin diseases, depression, premature labour, glaucoma and conditions in which there is an advantage in lowering gastric acidity, particularly in gastric and peptic ulceration.

The invention thus further provides compounds of formula (I) and their physiologically acceptable salts for use as an active therapeutic agent in particular for the treatment of conditions subject to amelioration by a compound possessing selective stimulant action at β$_2$-adrenoreceptors, for example diseases associated with reversible airways obstruction.

In a further or alternative aspect there is provided a method for the treatment of a disease associated with reversible airways obstruction in a mammal including man comprising administration of an effective amount of a compound of formula (I) or a physiologically acceptable salt thereof for the manufacture of a medicament for the treatment of a condition which may be ameliorated by a compound having selective β$_2$-adrenoreceptor stimulant activity.

It will be appreciated by those skilled in the art that reference herein to treatment extends to prophylaxis as well as the treatment of established symptoms.

It is possible that a compound of the invention may be administered to a patient as the raw chemical, but it is preferable to present the active ingredient as a pharmaceutical formulation.

The invention accordingly provides a pharmaceutical formulation comprising a compound of formula (I) or a physiologically acceptable salt thereof together with one or more physiologically acceptable carriers and, optionally, other therapeutic and/or prophylactic ingredients. The carrier(s) must be "acceptable" in the sense of being compatible with the other ingredients of the formulation and not deleterious to the recipient thereof.

The compounds may be formulated in a form suitable for administration by inhalation or insufflation, or for oral, buccal, parenteral, topical (including nasal) or rectal administration. Administration by inhalation or insufflation is preferred.

For administration by inhalation the compounds according to the invention are conveniently delivered in the form of an aerosol spray presentation from pressurised packs, with the use of a suitable propellant, such as dichlorodifluoromethane, trichlorofluoromethane, dichlorotetraflurorethane, carbon dioxide or other suitable gas, or from a nebuliser. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in for example capsules or cartridges of e.g. gelatin, or blister packs from which the powder may be administered with the aid of an inhaler or insufflator.

For oral administration, the pharmaceutical composition may take the form of, for example, tablets, capsules, powders, solutions, syrups or suspensions prepared by conventional means with acceptable excipients.

For buccal administration the composition may take the form of tablets, drops or lozenges formulated in the conventional manner.

The compounds of the invention may be formulated for parenteral administration by bolus injection or continuous infusion. Formulation for injection may be presented in unit dosage form in ampoules, or in multi-dose containers with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution with a suitable vehicle, e.g. sterile pyrogen-free water, before use.

For topical administration the pharmaceutical composition may take the form of ointments, lotions or creams formulated in a conventional manner, with for example an aqueous or oily base, generally with the addition of suitable thickening agents and/or solvents. For nasal application, the composition may take the form of a spray, formulated for example as an aqueous solution or suspension or as an aerosol with the use of a suitable propellant.

The compounds of the invention may also be formulated in rectal compositions such as suppositories or retention enemas, e.g. containing conventional suppository bases such as cocoa butter or other glyceride.

Where pharmaceutical compositions are described above for oral, buccal, rectal or topical administration, these may be presented in a conventional manner associated with controlled release forms.

A proposed daily dosage of active compound for the treatment of man is 0.005 mg to 100 mg, which may be conveniently administered in one or two doses. The precise dose employed will of course depend on the age and condition of the patient and on the route of administration. Thus a suitable dose for administration by inhalation is 0.005 mg to 20 mg, for oral administration is 0.02 mg to 100 mg, and for parenteral administration is 0.01 mg to 2 mg for administration by bolus injection and 0.01 mg to 25 mg for administration by infusion.

The compounds according to the invention may be prepared by any process known in the art for the preparation of compounds of analogous structure. In the following description, $R^1$, $R^2$, X, Y, W and A are as defined for general formula (I) unless otherwise specified.

In one general process (A), a compound of general formula (I) in which $R^1$ is a hydrogen atom may be prepared by alkylation. Conventional alkylation procedures may be used.

Thus, for example, in one alkylation process (a), a compound of general formula (I) in which $R^1$ is a hydrogen atom may be prepared by alkylation of an amine of general formula (II):

(wherein $R^8$ represents a hydrogen atom or a protecting group and $R^9$ represents a hydrogen atom) followed by removal of any protecting groups where present.

The alkylation (a) may be effected using an alkylating agent of general formula (III):

(wherein L is a leaving group, for example a halogen atom such as chlorine, bromine or iodine, or a hydrocarbylsulphonyloxy group such as methanesulphonyloxy or p-toluenesulphonyloxy).

The alkylation is preferably effected in the presence of a suitable acid scavenger, for example inorganic bases such as sodium or potassium carbonate, organic bases such as triethylamine, diisopropylethylamine or pyridine, or alkylene oxides such as ethylene oxide or propylene oxide. The reaction is conveniently effected in a solvent such as acetonitrile or an ether e.g. tetrahydrofuran, a ketone e.g. butanone, a substituted amide e.g. dimethylformamide or a chlorinated hydrocarbon e.g. chloroform, at a temperature between ambient and the reflux temperature of the solvent.

According to another example (b) of an alkylation process, a compound of general formula (I) in which $R^1$ represents a hydrogen atom may be prepared by alkylation of an amine of general formula (II), as previously defined except that $R^9$ is a hydrogen atom or a group convertible thereto under the reaction conditions, with a compound of general formula (IV):

in the presence of a reducing agent, followed when necessary by removal of any protecting groups.

Examples of suitable $R^9$ groups convertible into a hydrogen atom are arylmethyl groups such as benzyl, α-methylbenzyl and benzhydryl.

Suitable reducing agents include hydrogen in the presence of a catalyst such as platinum, platinum oxide, palladium, palladium oxide, Raney nickel or rhodium, on a support such as charcoal, using an alcohol, e.g. ethanol or methanol, or an ester, e.g. ethyl acetate, or an ether, e.g. tetrahydrofuran, or water, as reaction solvent, or a mixture of solvents, e.g. a mixture of two or more of those just described, at normal or elevated temperature and pressure, for example from 20° to 100° C. and from 1 to 10 atmospheres.

Alternatively when one or both of $R^8$ and $R^9$ are hydrogen atoms, the reducing agent may be a hydride such as diborane or a metal hydride such as sodium borohydride, sodium cyanoborohydride or lithium aluminium hydride. Suitable solvents for the reaction with these reducing agents will depend on the particular hydride used, but will include alcohols such as methanol or ethanol, or ethers such as diethyl ether or tetrahydrofuran.

When a compound of formula (II) where $R^8$ and $R^9$ are each hydrogen atoms is used, the intermediate imine of formula (V) may be formed:

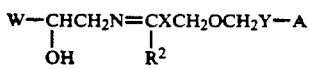

(V)

Reduction of the imine using the conditions described above, followed, where necessary, by removal of any protecting groups gives a compound of general formula (I).

In another general process (B) compounds of formula (I) may be prepared by reducing an intermediate of general formula (VI):

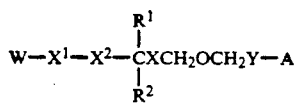

(VI)

wherein at least one of $X^1$, $X^2$, X and Y represents a reducible group and the other(s) take the appropriate meaning as follows, which is $X^1$ is —CH(OH)—, $X^2$ is —CH$_2$NR$^8$— (where $R^8$ represents a hydrogen atom or a protecting group), and X and Y are as defined in formula (I), followed where necessary by the removal of any protecting groups.

Suitable reducible groups include those wherein $X^1$ is a group > C=O, $X^2$ is a group —CH$_2$NR$^{10}$— (wherein $R^{10}$ represents a group convertible to hydrogen by catalytic hydrogenation, for example an arylmethyl group such as benzyl, benzhydryl or α-methylbenzyl), or —CONH—, X is an alkenylene or alkynylene group, Y is an alkenylene or alkynylene group.

The reduction may be effected using reducing agents conveniently employed for the reduction of ketones, amides, protected amines, alkenes and alkynes.

Thus, for example, when $X^1$ in general formula (II) represents a > C=O group this may be reduced to a —CH(OH)— group using hydrogen in the presence of a catalyst such as platinum, platinum oxide, palladium palladium oxide, Raney nickel or rhodium, on a support such as charcoal, using an alcohol e.g. ethanol, an ester e.g. ethyl acetate, an ether e.g. tetrahydrofuran, or water, as reaction solvent, or a mixture of solvents, e.g. a mixture of two or more of those just described, at normal or elevated temperature and pressure, for example from 20° to 100° C. and from 1 to 10 atmospheres. Alternatively, the reducing agent may be, for example, a hydride such a diborane or a metal hydride such as lithium aluminium hydride, sodium bis(2-methoxyethoxy) aluminium hydride, sodium borohydride or aluminium hydride. The reaction may be effected in an appropriate solvent, such as an alcohol e.g. methanol or ethanol, or an ether such as tetrahydrofuran, or a halogenated hydrocarbon such as dichloromethane.

When $X^2$ in general formula (VI) represents a —CH$_2$NR$^{10}$— group this may be reduced to a —CH$_2$NH— group using hydrogen in the presence of a catalyst as described above.

When $X^2$ in general formula (VI) represents a —CONH— group, this may be reduced to a group —CH$_2$NH$_2$— using a hydride such a diborane or a complex metal hydride such as lithium aluminium hydride in a solvent such as an ether e.g. tetrahydrofuran or diethyl ether.

When X and/or Y in general formula (VI) represents an alkenylene or alkynylene group, this may be reduced to an alkylene group using hydrogen in the presence of a catalyst as described above. Alternatively, when X and/or Y represents an alkynylene group, this may be converted to an alkenylene group, using for example hydrogen and a lead-poisoned palladium on calcium carbonate catalyst in a solvent such as pyridine, or lithium aluminium hydride in a solvent such as diethyl ether at low temperature.

Where it is desired to use a protected intermediate of general formula (VI) it is particularly convenient to use protecting groups which are capable of being removed under the reducing conditions, for example hydrogen and a catalyst, thus avoiding the need for a separate deprotection step. Suitable protecting groups of this type include arylmethyl groups such as benzyl, benzhydryl and α-methylbenzyl.

In the above reduction process, and also in the preparation of intermediates, care must be taken to avoid the use of hydrogen and a catalyst when products are required in which X and/or Y represent alkenylene or alkynylene groups.

In a further process (C) compounds of formula (I) may be prepared by deprotecting an intermediate of general formula (VII):

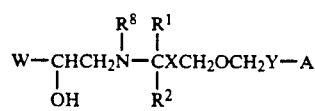

(VII)

wherein $R^8$ is a protecting group and/or W contains a protecting group(s).

The protecting group may be any conventional protecting group as described for example in "Protective Groups in Organic Synthesis", by Theodora Greene (John Wiley and Sons Inc, 1981). Thus, for example, hydroxyl groups may be protected by arylmethyl groups such as benzyl, diphenylmethyl or triphenylmethyl, by acyl groups such a acetyl, or as tetrahydropyranyl derivatives. Examples of suitable amino protecting groups include arylmethyl groups such as benzyl, α-methylbenzyl, diphenylmethyl or triphenylmethyl, and acyl groups such as acetyl, trichloroacetyl or trifluoroacetyl.

The deprotection to yield a compound of general formula (I) may be effected using conventional techniques. Thus for example arylmethyl groups may be removed by hydrogenolysis in the presence of a metal catalyst (e.g. palladium on charcoal). Tetrahydropyranyl groups may be cleaved by hydrolysis under acidic conditions. Acyl groups may be removed by hydrolysis with an acid such as mineral acid e.g. hydrochloric acid, or a base such as sodium hydroxide or potassium carbonate, and a group such as trichloroacetyl may be removed by reduction with, for example, zinc and acetic acid.

Intermediates of formula (VI) for use in the reduction process (B) in which $X^1$ is the group >C=O may be prepared by reaction of a haloketone of formula (VIII)

(VIII)

(where Hal represents a halogen atom e.g. bromine) with an amine of formula (IX)

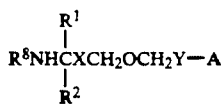

(where R[8] is a hydrogen atom or a group convertible thereto by catalytic hydrogenation).

The reaction may be effected in a cold or hot solvent, for example tetrahydrofuran, dioxan, chloroform, dichloromethane, dimethylformamide, acetonitrile, a ketone such as butanone or an ester such as ethyl acetate, preferably in the presence of a base such as diisopropylethylamine, sodium carbonate or other acid scavenger such as propylene oxide.

It is convenient not to purify the intermediates of formula (VI) formed by reaction of a haloketone of formula (VIII) with an amine of formula (IX), but to reduce the crude reaction product to give a compound of formula (I).

Amines of formula (II) and haloketones of formula (VIII) are either known compounds or may be prepared by methods analogous to those described for the preparation of known compounds.

Suitable methods for preparing intermediates of formulae (III), (IV), (V) and (VI) are described in the exemplification included hereinafter.

In the general processes described above, the compound of formula (I) obtained may be in the form of a salt, conveniently in the form of a physiologically acceptable salt. Where desired, such salts may be converted to the corresponding free bases using conventional methods.

Physiologically acceptable salts of the compounds of general formula (I) may be prepared by reacting a compound of general formula (I) with an appropriate acid or base in the presence of a suitable solvent such as acetonitrile, acetone, chloroform, ethyl acetate or an alcohol, e.g. methanol, ethanol or isopropanol.

Physiologically acceptable salts may also be prepared from other salts, including other physiologically acceptable salts, of the compounds of general formula (I), using conventional methods.

When a specific enantiomer of a compound of general formula (I) is required, this may be obtained by resolution of a corresponding racemate of a compound of general formula (I) using conventional methods.

Thus, in one example an appropriate optically active acid may be used to form salts with the racemate of a compound of general formula (I). The resulting mixture of isomeric salts may be separated for example by fractional crystallisation, into the diastereoisomeric salts from which the required enantiomer of a compound of general formula (I) may be isolated by conversion into the required free base.

Alternatively, enantiomers of a compound of general formula (I) may be synthesised from the appropriate optically active intermediates using any of the general processes described herein.

Specific diastereoisomers of a compound of formula (I) may be obtained by conventional methods for example, by synthesis from an appropriate asymmetric starting material using any of the processes described herein, or by conversion of a mixture of isomers of a compound of general formula (I) into appropriate diastereoisomeric derivatives e.g. salts which then can be separated by conventional means e.g. by fractional crystallisation.

The following examples illustrate the invention. Temperatures are in °C. 'Dried' refers to drying using magnesium sulphate or sodium sulphate. Unless otherwise stated, thin layer chromatography (t.l.c.) was carried out on silica and flash column chromatography (FCC) on silica (Merck 9385). The following solvent systems may be used: System A—toluene:ethanol:0.88 ammonia; System B—ethyl acetate:methanol:0.88 ammonia; System C—toluene: ethanol: triethylamine; System D—ether:cyclohexane. The following abbreviations are used: THF—tetrahydrofuran, TAB—tetra-n-butylammonium hydrogen sulphate, DMF—dimethylformamide.

EXAMPLE 1

$\alpha^1$-[[[6-2-Cyclopentylethoxy)hexyl]amino]methyl]-4-hydroxy-1,3-benzenedimethanol, compound with water (1:0.23)

(a) [2-[(6-Bromohexyl)oxy]ethyl]cyclopentane

2-Cyclopentylethanol (2.4 g), 1,6-dibromohexane (9.5 g), TAB (0.94 g) and aqueous sodium hydroxide solution (12.5M, 32 ml) were stirred at room temperature overnight. The reaction mixture was poured into water (100 ml) and extracted with ether (3×100 ml). The ethereal extracts were dried and evaporated. The residue was purified by FCC eluting with System D (1:0 to 1:49). The resulting oil was distilled to give (1a) (3.21 g) b.p. 150°/0.15 Torr.

(b) $\alpha^1$-[[[6-(2-Cyclopentylethoxy)hexyl]amino]methyl]-4-hydroxy-1,3-benzenedimethanol, compound with water (1:0.23)

$\alpha^1$-(Aminomethyl)-4-hydroxy-1,3-benzenedimethanol (1.43 g), (1a) (1.80 g) and N,N-diisopropylethylamine (1.64 ml) in DMF (20 ml) were stirred under nitrogen at 100° for 1 h. The cooled mixture was poured into saturated aqueous sodium bicarbonate solution (80 ml) and extracted with ethyl acetate (2×100 ml). The extracts were washed with water, dried and evaporated. The residue was purified by FCC eluting with System B (89:10:1) to give the title compound (788 mg).

Analysis found C,68.9; H,9.95; N,3.55; $C_{22}H_{37}NO_4.0.23H_2O$ requires C,68.85; H,9.85; N,3.65%.

EXAMPLE 2

$\alpha^1$-[[[6-(Cyclohexylmethoxy)hexyl]amino]methyl]-4-hydroxy-1,3-benzenedimethanol (a) [(6-Bromohexyl)oxy]methylcyclohexane From cyclohexylmethanol (5.0 g) and 1,6-dibromohexane (20 ml) by the method of (1a) to give (2a) (7.78 g) b.p. 182°/0.8 Torr.

(b) $\alpha^1$-[[[6-(Cyclohexylmethoxy)hexyl]amino]methyl]-4-hydroxy-1,3-benzenedimethanol From $\alpha^1$-(aminomethyl)-4-hydroxy-1,3-benzenedimethanol (1.00 g) and (2a) (1.26 g) by the method of (1b). FCC eluting with ethyl acetate/methanol, 19:1 to 9:1, gave an oil (0.53 g) which crystallised from ethyl acetate to give the title compound mp 72°–74°.

Analysis Found: C,69.55; H,10.15; N,3.7; $C_{22}H_{37}NO_4$ requires C,69.6; H,9.85; N,3.7%.

EXAMPLE 3

$\alpha^1$-[[[6-[2(Cyclohexyl)ethoxy]hexyl]amino]methyl]-4-hydroxy-1,3-benzenedimethanol (a) [2-[(6-Bromohexyl)oxy]ethyl]cyclohexane From 2-cyclohexylethanol (12 g) and 1,6-dibromohexane (43 ml) by the method of (1a) to give (3a) (20 g) t.l.c. (hexane) Rf 0.5.

(b) N-[6-2-(Cyclohexyl)ethoxy]hexyl]benzenemethanamine

A solution of (3a) (12 g) and benzylamine (40 ml) was heated at 140° for 2 h. 2N Hydrochloric acid (200 ml) was added and the mixture extracted with ethyl acetate (2×200 ml). The organic extacts were washed with sodium bicarbonate solution (500 ml), dried and concentrated to give an oil which was purified by FCC eluting with System C, 98:2:1 to give 3b (10 g).

Analysis Found: C,79.8; H,11.2; N,4.4; $C_{21}H_{35}NO$ requires C,79.4; H,11.1; N,4.4%.

(c) $\alpha^1$-[[[6-[2(Cyclohexyl)ethoxy]hexyl]amino]methyl]-4-hydroxy-1,3-benzenedimethanol A solution of (3b) (4.2 g), 2-bromo-1-[4-hydroxy-3-(hydroxymethyl) phenyl]ethanone (3.4 g) and N,N-diisopropylethylamine (3.6 g) in THF (20 ml) was allowed to stand at room temperature under nitrogen for 22 h. The mixture was filtered and the filtrate evaporated to give an oil which was dissolved in ethanol (30 ml) and hydrogenated over pre-reduced 5% platinum oxide on charcoal (800 mg) and 10% palladium oxide on charcoal (800 mg) in ethanol (10 ml). The mixture was filtered and evaporated to give a foam. Purification by FCC eluting with System A (80:20:1) gave a yellow oil which was triturated under ether/hexane (1:1) to give the title compound (3.2 g) m.p. 42°–45°.

Analysis Found: C,68.5; H,9.8; N,3.5; $C_{23}H_{39}NO_4.0.5 H_2O$ requires C,68.6; H,10.0; N,3.5%.

EXAMPLE 4

$\alpha^1$-[[[6-[(3-Ethylpentyl)oxy]hexyl]amino]methyl]-4-hydroxy-1,3-benzenedimethanol (a) 1-Bromo-6-[(3-ethylpentyl)oxy]hexane From 3-ethyl-1-pentanol (1.5 g) and 1,6-dibromohexane (5.95 ml) by the method of (1a) to give (4a) (2.16 g).

Analysis Found C,56.05; H,10.1; Br, 28.85; $C_{13}H_{27}BrO$ requires C,55.9; H,9.75; Br, 28.6%.

(b) $\alpha^1$-[[[6-[(3-Ethylpentyl)oxy]hexyl]amino]methyl]-4-hydroxy-1,3-benzenedimethanol From (4a) (0.97 g) and $\alpha^1$-(aminomethyl)-4-hydroxy-1,3-benzenedimethanol (1.16 g) by the method of (1b). Purification was by FCC eluting with ethyl acetate/methanol/triethylamine (90:10:1) to give the title compound (135 mg), t.l.c. (ethyl acetate/methanol/triethylamine, 90:10:1) Rf 0.25.

Analysis Found: C,69.25; H,10.7; N,3.7; $C_{22}H_{39}NO_4$ requires C,69.25; H,10.3; N,3.65%.

EXAMPLE 5

$\alpha^1$-[[[6-[4,4-Dimethylpentyl)oxy]hexyl]amino]methyl]-4-hydroxy-1,3-benzenedimethanol (a) 1-Bromo-6-[(4,4-dimethylpentyl)oxy]hexane From 4,4-dimethyl-1-pentanol (1.5 g) and 1,6-dibromohexane (5.95 ml) by the method of (1a) to give (5a) (2.57 g) t.l.c. (System D, 1:79) Rf 0.36.

(b) $\alpha^1$-[[[61[4,4-Dimethylpentyl)oxy]hexyl]amino]methyl]-4-hydroxy-1,3-benzenedimethanol From $\alpha^1$-(aminomethyl)-4-hydroxy-1,3-benzenedimethanol (1.44 g) and (5a) (2.0 g) by the method of (1b). Purification was by FCC elutng with ethyl acetate/methanol/triethylamine (90:10:1) to give an oil which on trituration with cyclohexane gave the title compound (339 mg) as a white solid m.p. 64.5°–66°.

Analysis Found: C,69.25; H,10.45; N,3.6; $C_{22}H_{39}NO_4$ requires C,69.25; H,10.3; N,3.65%.

EXAMPLE 6

$\alpha^1$-[[[6-[(Hexyl)oxy]hexyl]amino]methyl]-4-hydroxy-1,3-benzenedimethanol benzoate (1:1) salt (a) [(6-Bromohexyl)oxy]hexane From hexanol (5 g) and 1,6-dibromohexane (22 ml) by the method of (1a) to give (6a) (10.5 g) t.l.c. (hexane) Rf 0.8.

(b) N-[6-[Hexyl)oxy]hexyl]benzenemethamamine

From (6a) (5 g) and benzylamine (15 ml) by the method of (3b) to give Example 6(b) (5.5 g) t.l.c. (System A, 80.20:1) Rf 0.65.

(c) $\alpha^1$-[[[6-[(Hexyl)oxy]hexyl]amino]methyl]-4-hydroxy-1.3-benzenedimethanol benzoate (1:1) (salt)

A solution of (6b) (2.2 g) 2-bromo-1-[4-hydroxy-3-(hydroxymethyl)phenyl]ethanone (1.8 g) and N,N-diisopropylamine (1.9 g) was allowed to stand at room temp. under nigrogen for 22 h. The mixture was filtered and the filtrate was evaporated to give an oil, a solution of which in ethanol (50 ml) was hydrogenated over prereduced 10% palladium oxide on charcoal (50% aqueous paste, 700 mg) and 5% platinum oxide on charcoal (800 mg). The mixture was filtered and evaporated. Purification by FCC eluting with System C (95:5:1) gave an oil (1.49 g) which was dissolved in methanol and treated with benzoic acid (488 mg) to give the title compound as a brown solid (1.8 g) m.p. 101°–103°.

Analysis Found: C,66.4; H,8.9; N,2.9. $C_{21}H_{37}NO_4C_7H_3O_2H_2O$ requires C,66.2; H,8.9; N,2.8%.

EXAMPLE 7

N-[5-[[[6-[2-(Cyclohexyl)ethoxy]hexyl]amino]-1-hydroxyethyl]-2-hydroxyphenyl]methanesulphonamide From (3b) (3.3 g) and N-[5-(bromoacetyl)-2-(phenylmethoxy)phenyl]methanesulphonamide (4.5 g) by the method of (3c) to give the title compound (2.5 g) as a white solid m.p.99°–101°.

Analysis Found: C,60.3; H,8.5; N,6.1; S,6.6; $C_{23}H_{40}N_2O_5S$ requires C,60.5; H,8.8; N,6.1; S,7.0%.

EXAMPLE 8

N-[2-Hydroxy-5-[2-[[6-[(3-ethylpentyl)oxy]hexyl]amino]-1-hydroxyethyl]phenyl]methanesulphonamide (a) N-[6-[(3-Ethylpentyl)oxy]hexyl]benzenemethanamine From 1-[(6-bromohexyl)oxy]-3-ethylpentane (1.5 g) and benzylamine (10 ml) by the method of (3b) to give (8a) (1.2 g) t.l.c. (System C, 80:20:1) Rf 0.6.

(b) N-[2-Hydroxy-5-[2-[[6-[(3-ethylpentyl)oxy]hexyl]amino]-1-hydroxyethyl]phenyl]methanesulphonamide From (8a) (1.0 g) and N-[5-(bromoacetyl)-2-(phenylmethoxy)phenyl]methanesulphonamide (1.3 g) by the method of (3c) to give the title compound (500 mg) as a white solid m.p. 69°–71°.

Analysis Found: C,59.4; H,8.7; N,6.1; S,6.9; $C_{22}H_{40}N_2SO_5$ requires C,59.4; H,9.1; N,6.3; S,7.2%.

EXAMPLE 9

$\alpha^1$-[[[6-(Heptyloxy)hexyl]amino]methyl]-4-hydroxy-1,3-benzenedimethanol (a) 1-[(6-Bromohexyl)oxy]-heptane From 1-heptanol (2.50 g) and 1.6-dibromohexene (15.74 g) by the method of (1a) to give (9a) (4.02 g) t.l.c. (System D, 1:79) Rf 0.33.

(b) α¹-[[[6-(Heptyloxy)hexyl]amino]methyl]-4-hydroxy-1,3-benzenedimethanol

From α¹-(aminomethyl)-4-hydroxy-1,3-benzenedimethanol (1.35 g) and (9a) (1.00 g) by the method of (1b). Purification was by FCC eluting with ethyl acetate/methanol/triethylamine (90:10:1) to give an oil which on trituratution with ether gave the title compound (357 mg) as a white solid m.p. 72°-74°.

Analysis Found: C,68.9; H,10.5; N,3.6; $C_{22}H_{39}NO_4$ requires C,69.25; H,10.3; N,3.65%.

EXAMPLE 10

4-Hydroxy-α¹-[[[6-[5-methylhexyl)oxy]hexyl]amino]methyl]-1,3-benzenedimethanol (a) 1-[(6-Bromohexyl)oxy]-5-methylhexane From 5-methyl-1-hexanol (1.00 g) and 1,6-dibromohexane (4.0 mg) by the method of (1a) to give (10a) (1.75 g) t.l.c. (ethyl acetate/cyclohexane, 1:79) Rf 0.15.

(b) 4-Hydroxy-α¹-[[[6-[(5-methylhexyl)oxy]hexyl]amino]methyl]-1,3-benzenedimethanol From α¹-(aminomethyl)-4-hydroxy-1,3-benzenedimethanol (1.18 g) and (10a) (0.99 g) by the method of (1b). Purification was by FCC eluting with ethyl acetate/methanol/triethylamine (90:10:1) to give an oil which was triturated with ether to give the title compound (192 mg) as a white solid m.p. 65°-67°.

Analysis Found: C,69.4; H,10.6; N,3.75; $C_{22}H_{39}NO_4$ requires C,69.25; H,10.3; N,3.65%.

EXAMPLE 11

4-Amino-3,5-dichloro-α-[[[6-(4-propoxybutoxy)hexyl]amino]methyl]benzenemethanol (a) 1-Bromo-6-(4-propoxybutoxy)hexane From 4-propoxybutanol (1.50 g) and 1,6-dibromohexane (5.1 ml) by the method of (1a) to give (11a) (2.08 g) t.l.c. (hexane/ether, 4:1) Rf 0.19.

(b) N-[6-(4-Propoxybutoxy)hexyl]benzenemethamine

From (11a) (2.03 g) and benzylamine (6 ml) by the method of (3b) to give (11b) (2.03 g) t.l.c. (System A, 39:10:1) Rf 0.45.

(c) 4-Amino-3,5-dichloro-α-[[(phenylmethyl)[6-(4-propoxybutoxy)hexyl]amino]methyl]benzenemethanol A mixture of 1-(4-amino-3,5-dichlorophenyl)-2-bromoethanone (1.49 g), (11b) (1.65 g), and N,N-diisopropylethylamine (1 ml) in THF (20 ml) was allowed to stand for 4 h, then filtered. The filtrate was evaporated to an oil, a solution of which in methanol (40 ml) was cooled to 0°-5° and sodium borohydride (800 mg) added portionwise over 0.5 h. After 1 h at 20°, the solution was evaporated and the residue partitioned between water (100 ml) and ethyl acetate (100 ml). The organic phase was dried and evaporated and the residue purified by FCC eluting with cyclohexane-ethyl acetate-triethylamine (66:33:1-50:49:1) to give the title compound as a colourless oil (2.62 g). T.l.c. (Et₃N, hexane-Et₂O 1:1) Rf 0.42.

(d) 4-Amino-3,5-dichloro-α-[[[6-(4-propoxybutoxy)hexyl]amino]methyl]benzenemethanol A solution of (11c) (2.63 g) in ethanol (100 ml) containing concentrated hydrochloric acid-ethanol (1:9, 4.55 ml) was added to a pre-hydrogenated suspension of 10% palladium on charcoal (1.02 g, 50% aqueous paste) in ethanol (30 ml) and hydrogenated for 5 minutes. The mixture was filtered, the filtrate was evaporated and the residue partitioned between 8% sodium bicarbonate solution (25 ml) and ethyl acetate (100 ml). The organic phase was dried and evaporated to an oil which was purified by FCC with System C (94:5:1-89:10:1) eluant to afford an oil. The oil was triturated with hexane to afford the title compound as a colourless powder (1.26 g) m.p. 51°-53°.

Analysis found C,57.7; H,8.35; N,6.3; Cl,16.4. $C_{21}H_{36}Cl_2N_2O_3$ requires C,57.9; H,8.3; N,6.4; Cl,16.3%.

EXAMPLE 12

4-Amino-α-[[[6-(3-butoxypropoxy)hexyl]amino]methyl]-3,5-dichloro benzenemethanol (a) 1-Bromo-6-(3-butoxypropoxy)hexane From 3-butoxy-1-propanol (3.0 g) and 1,6-dibromohexane (10.5 ml) by the method of (1a) to give (12a) (3.7 g) t.l.c. (hexane/ether, 4:1) Rf 0.39.

(b) N-[6-(3-Butoxypropoxy)hexyl]benzenemethanamine

From (12a) (3.7 g) and benzylamine (15 ml) by the method of (3b) to give (12b) (3.6 g) t.l.c. (System A, 90:10:1) Rf 0.56.

(c) 4-Amino-3,5-dichloro-α-[[[6-(3-butoxypropoxy)hexyl](phenylmethyl)amino]methyl]benzenemethanol From 1-(4-amino-3,5-dichlorophenyl)-2-bromoethanone (1.8 g) and (12b) (2.0 g) by the method of (11c) to give (12c) (1.9 g) t.l.c. (System A, 90:10:1) Rf 0.70.

(d) 4-Amino-α-[[[6-(3-butoxypropoxy)hexyl]amino]methyl]-3,5-dichlorobenzenemethanol From Example (12c) (1.8 g) by the method of (11d). Purification was by FCC eluting with System A (98:2:1) to give the title compound (1.2 g) as a white solid m.p. 49°-51°.

Analysis found C,58.0; H,8.4; N,6.3; Cl,16.4; $C_{21}H_{36}Cl_2N_2O_3$ found C,57.9; H,8.3; N,6.4; Cl,16.3%.

We claim:

1. A compound of the formula (I)

W—CHOHCH₂NH(CH₂)₆OCH₂Y—A or a physiologically acceptable salt of solvate thereof; wherein: Y represents a direct bond or a $C_{1-6}$alkylene group; and A represents a $C_{1-6}$alkoxy group, with the proviso that the sum total of carbon atoms in Y and A is not less than 5; and W represents a group

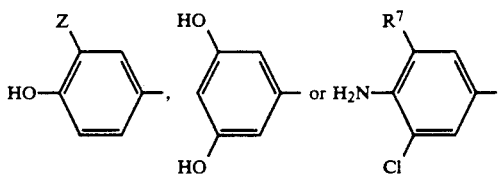

wherein Z represents a group $R^3(CH_2)_q$ where q is 0, 1 or 2 and $R^3$ is a group $R^4CONH—$, $R^4NHCONH—$, $R^4R^5NSO_2NH—$, $R_6SO_2NH—$ or $—OH$; $R^4$ and $R^5$ each represent a hydrogen atom or a $C_{1-3}$alkyl group; $R^6$ represents a $C_{1-3}$alkyl group; $R^7$ represents a chlorine atom or the group $—CF_3$.

2. A compound according to claim 1, in which the carbon atom in the $—CH(OH)—$ group is in the R configuration.

3. A compound according to claim 1, in which W represents a group

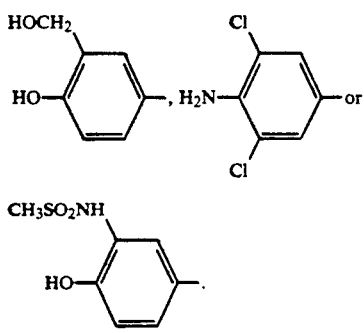

4. A compound according to claim 1, in which W represents a group

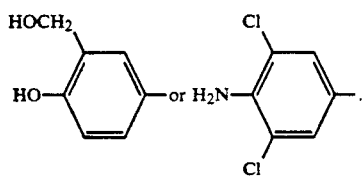

5. A compound according to claim 1, of the formula

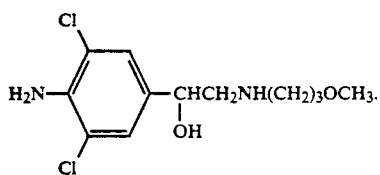

6. A compound according to claim 5 wherein Y represents —(CH$_2$)$_3$— or —(CH$_2$)$_4$—.

7. A compound according to claim 6 wherein Y represents —(CH$_2$)$_3$—.

8. A compound according to claim 5 wherein A represents —O(CH$_2$)$_2$CH$_3$ or —O(CH$_2$)$_3$CH$_3$.

9. A compound according to claim 8 wherein A represents —O(CH$_2$)$_3$CH$_3$.

10. A compound according to claim 5 selected from the group consisting of 4-amino-3,5-dichloro-α-[[[6-(4-propoxybutoxy)hexyl]amino]methyl]benzenemethanol; 4-amino-3,5-dichloro-α[[[6-(3-butoxypropoxy)hexyl]amino]methyl]benzenemethanol; or a physiologically acceptable salt and solvate thereof.

11. A pharmaceutical composition for the treatment of a disease associated with reversible airways obstruction or for the treatment of a condition selected from inflammatory and allergic skin disease, depression, premature labour, glaucoma, and gastric and peptic ulceration which comprises an effective amount to relieve said disease or condition of at least one compound of formula (I) as defined in claim 1 or a physiologically acceptable salt or solvate thereof together with one or more physiologically acceptable carriers or excipients.

12. A pharmaceutical composition according to claim 11 adapted for administration by inhalation or insufflation.

13. A pharmaceutical composition according to claim 12 which is formulated in unit dosage form comprising 0.005 mg to 20 mg of active ingredient.

14. A pharmaceutical composition for the treatment of a disease associated with reversible airways obstruction or for the treatment of a condition selected from inflammatory and allergic skin disease, depression, premature labour, glaucoma, and gastric and peptic ulceration which comprises an effective amount to relieve said disease or condition of at least one compound of formula (I) as defined in claim 5 or a physiologically acceptable salt or solvate thereof together with one or more physiologically acceptable carriers or excipients.

15. A pharmaceutical composition according to claim 14 adapted for administration by inhalation or insufflation.

16. A pharmaceutical composition according to claim 15 which is formulated in unit dosage form comprising 0.005 mg to 20 mg of active ingredient.

17. A method of treating a disease associated with reversible airways obstruction which comprises administering to a patient an effective amount to relieve said disease of at least one compound of formula (I) as defined in claim 1 or a physiologically acceptable salt or solvate thereof.

18. A method according to claim 17 wherein said disease is asthma or chronic bronchitis.

19. A method of treating a condition selected from inflammatory and allergic skin disease, depression, premature labour, glaucoma, and gastric and peptic ulceration which comprises administering to a patient an effective amount to relieve said condition of at least one compound of formula (I) as defined in claim 1 or a physiologically acceptable salt or solvate thereof.

20. A method of treating a disease associated with reversible airways obstruction which comprises administering to a patient an effective amount to relieve said disease of a pharmaceutical composition according to claim 1.

21. A method according to claim 20 wherein said disease is asthma or chronic bronchitis.

22. A method of treating a condition selected from inflammatory and allergic skin disease, depression, premature labour, glaucoma, and gastric and peptic ulceration which comprises administering to a patient an effective amount to relieve said condition of a pharmaceutical composition according to claim 11.

23. A method of treating a disease associated with reversible airways obstruction which comprises administering to a patient an effective amount to relieve said disease of at least one compound of formula (I) as defined in claim 5 or a physiologically acceptable salt or solvate thereof.

24. A method according to claim 23 wherein said disease is asthma or chronic bronchitis.

25. A method of treating a condition selected from inflammatory and allergic skin disease, depression, premature labour, glaucoma, and gastric and peptic ulceration which comprises administering to a patient an effective amount to relieve said condition of at least one compound of formula (I) as defined in claim 5 or a physiologically acceptable salt or solvate thereof.

26. A method of treating a disease associated with reversible airways obstruction which comprises administering to a patient an effective amount to relieve said disease of a pharmaceutical composition according to claim 12.

27. A method according to claim 26 wherein said disease is asthma or chronic bronchitis.

28. A method of treating a condition selected from inflammatory and allergic skin disease, depression, premature labour, glaucoma, and gastric and peptic ulceration which comprises administering to a patient an effective amount to relieve said condition of a pharmaceutical composition according to claim 14.

* * * * *

UNITED STATES PATENT AND TRADEMARK OFFICE
CERTIFICATE OF CORRECTION

PATENT NO. : 5,066,678

DATED : November 19, 1991

INVENTOR(S) : Ian F. Skidmore, et al.

It is certified that error appears in the above-identified patent and that said Letters Patent is hereby corrected as shown below:

Column 14, line 42, after the word "salt", change "of" to -- or --.

Column 15, line 31, change "$\underset{OH}{C}HCH_2NH(CH_2)_3OCH_3$" to "$\underset{OH}{C}HCH_2NH(CH_2)_6OCH_2Y\text{-}A$".

Signed and Sealed this

Fourteenth Day of December, 1993

*Attest:*

BRUCE LEHMAN

*Attesting Officer*     *Commissioner of Patents and Trademarks*